United States Patent
Zhong et al.

(10) Patent No.: US 7,453,274 B1
(45) Date of Patent: Nov. 18, 2008

(54) DETECTION OF DEFECTS USING TRANSIENT CONTRAST

(75) Inventors: Lei Zhong, Parker, TX (US); John Fretwell, Fort Worth, TX (US); Kara Lee Sherman, Santa Clara, CA (US); Robert William Fiordalice, Los Altos Hills, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 0 days.

(21) Appl. No.: 11/982,096

(22) Filed: Oct. 31, 2007

Related U.S. Application Data

(60) Provisional application No. 60/998,367, filed on Oct. 9, 2007.

(51) Int. Cl.
*G01R 31/305* (2006.01)
(52) U.S. Cl. .................. 324/751; 250/310; 250/311
(58) Field of Classification Search ................ 324/751, 324/158.1; 205/311, 310
See application file for complete search history.

(56) References Cited

U.S. PATENT DOCUMENTS

| | | | |
|---|---|---|---|
| 5,132,507 A * | 7/1992 | Nakano | 219/121.31 |
| 6,169,603 B1 * | 1/2001 | Takayama | 356/500 |
| 6,204,075 B1 | 3/2001 | Kikuchi | |
| 7,081,625 B2 * | 7/2006 | Furiki et al. | 250/310 |
| 7,132,301 B1 | 11/2006 | Fan | |
| 7,135,676 B2 * | 11/2006 | Nakasuji et al. | 250/310 |
| 7,244,923 B2 * | 7/2007 | Song et al. | 250/214.1 |

* cited by examiner

*Primary Examiner*—Ha Nguyen
*Assistant Examiner*—Richard Isla Rodas
(74) *Attorney, Agent, or Firm*—Okamoto & Benedicto LLP

(57) ABSTRACT

One embodiment relates to a method for detecting defects in circuitry formed on a semiconductor substrate. A first scan of said circuitry is performed by scanning a primary electron beam in a first scan direction relative to said circuitry, and secondary electrons emitted during the first scan are detected so as to form a first voltage-contrast image. A second scan of said circuitry is performed by scanning the primary electron beam in a second scan direction relative to said circuitry, and secondary electrons emitted during the second scan are detected so as to form a second voltage-contrast image. The second scan direction is non-parallel to the first scan direction. The first and second voltage-contrast images are then compared to detect electrically-active defects. Other embodiments, aspects and features are also disclosed.

13 Claims, 5 Drawing Sheets

DETECTION OF DEFECTS USING TRANSIENT CONTRAST

CROSS-REFERENCE TO RELATED APPLICATION

The present application claims the benefit of U.S. Provisional Patent Application No. 60/998,367 entitled "Detection Of Defects Using Transient Contrast", filed Oct. 9, 2007, by inventors Lei Zhong, John Fretwell, Kara Lee Sherman and Robert William Fiordalice, the disclosure of which is hereby incorporated by reference in its entirety.

BACKGROUND OF THE INVENTION

1. Field of the Invention

The present invention relates generally to electron beam systems. The present invention more particularly relates to voltage contrast detection of defective structures using scanning electron microscopes.

2. Description of the Background Art

The defects detected by a state-of-the art scanning electron microscope (SEM) inspection system may be divided roughly into two categories: local contrast (physical) defects; and voltage contrast defects.

For local contrast defects or physical defects, contrast formation is directly related to the emission of secondary and/or backscattering electrons from the defect in question. These defects are generally located at the positions where the contrast appears (in x, y, and z directions). Local contrast defects generally manifest themselves due to its chemistry (i.e. atomic number Z contrast) and/or geometric properties (i.e. topographic contrast).

For voltage contrast defects, contrast formation is due to the fact that the probability that secondary electrons escape from a specimen may be modulated substantially by the surface potential. A voltage contrast defect may be regarded as electrically active. The defect is electrically active in that it is capable of enabling electron bombardment to alter the electrostatic potential of the target in which the defect exists. Voltage contrast may be "long range" in that the contrast may appear at positions which are relatively far away from the actual physical location of the defect. Voltage contrast does not require direct interaction between the primary electron beam and the defect in question. This is because voltage contrast formation needs no involvement of electrons emitted directly from the defect.

The long-range character of voltage contrast defect detection plays a role in at least three aspects. First, the visibility of a voltage contrast defect is related to the defect's capability to help change the surface potential. The physical size of the defect becomes of less importance. As a consequence, defect detection with voltage contrast may be enhanced by system features other than higher resolution. Second, detection of subsurface defects is enabled by the spatial displacement of voltage contrast in the z-direction (the direction normal to the surface). This capability may be especially useful for a multi-layer structure, such as, for example, modern interconnect technology, where a substantial amount of defects are often formed in underlying layers. Third, the "long range" character of voltage contrast (i.e. the fact that direct interaction between the primary electron beam and the defect is not needed) makes it possible to inspect a device by scanning only a small percentage of the total area of interest. As a result of this aspect, voltage contrast defect detection may be used to accelerate (reduce the time needed to perform) inspection of a specimen. The specimen may be, for example, a semiconductor wafer with memory arrays or other circuitry thereon.

Hence, voltage contrast has capabilities and features which make it a useful and advantageous technique for detecting defects. Nevertheless, useful as it is, voltage contrast is often a complicated phenomenon to harness effectively.

A first complication or problem is that voltage contrast is a combined result of the escape probability of secondary electrons and the collection efficiency of the detector. Each of these two factors depend on surface potential distribution in its own way. This complicated dependency is exacerbated by the fact that the electric field on the specimen surface is rarely uniform and is to a large extent affected by the apparatus configuration. The transverse component of the electric field, which is usually non-zero, may often cause secondary electrons to accelerate in the direction parallel to the specimen surface so as to evade the detector altogether.

A second complication or problem is that additional failure analysis is typically needed to correlate a voltage contrast defect to an actual physical defect. For example, a missing via in copper interconnection technology may cause voltage contrast and so be detectable. However, it typically takes tedious failure analysis to confirm this defect because it lies beneath the surface.

At the transistor level, electrical failure may have many different mechanisms and current leakage may go through many different routes. Each leakage path may potentially generate the voltage contrast observed. Voltage contrast imaging typically results in a "mosaic" combining effects from various leakages. The defect of interest (DOI) or the leakage path of interest is typically either overwhelmed by the "background noise" effects from the defect population or may be undetectable.

Thus, applicants respectfully submit that it is desirable to provide a method to isolate the leakage path of interest while suppressing or filtering out the background noise from other defects. An advantageous goal of such a method is to make the defect detection more useful and reliable.

DETAILED DESCRIPTION

First, to understand charge build-up, let a specimen be exposed to an energetic primary electron beam. If the specimen is floating, charge build-up occurs whenever the electron influx and outflow are not equal.

Next, to understand voltage contrast, consider the impact of charge build-up on secondary electron yield. Because a secondary electron is typically of relatively low energy, the probability of the secondary electron escaping away from a specimen is strongly modulated by the surface voltage. Hence, the secondary electron yield is also strongly modulated by the surface voltage. Thus, voltage contrast is generally expected when there is a difference in surface voltage between neighboring regions or features on the specimen. For example, a target feature may have a surface voltage which is different from the surface voltage of the surrounding (background) area. In that case, voltage contrast would be expected between the target feature and the background area.

Figure 1A:
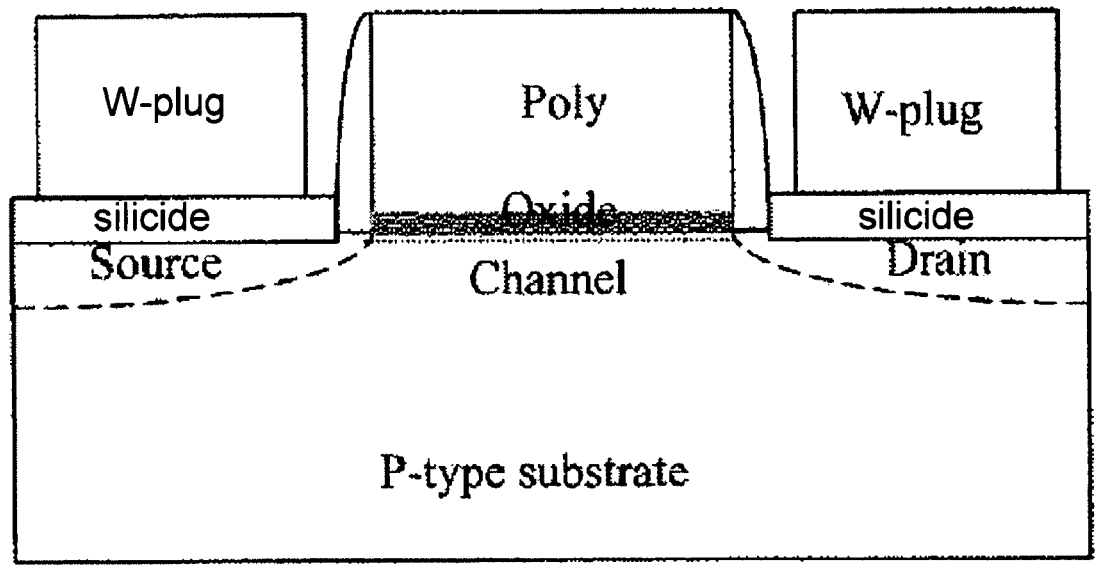
FIG. 1A is a cross-sectional diagram of a non-defective NMOS structure.

To understand how a defect typically leads to voltage contrast, consider a non-defective NMOS structure which is shown in FIG. 1A. The connectivity between source and drain through the channel is controlled by the gate stack. Contact to the source and drain is made through W-plugs (tungsten plugs) on a self-aligned silicide. When the specimen is exposed to an electron beam, charge build-up may occur on the W-plug because it is floating (i.e. not grounded). The build-up consequently leads to surface voltage change.

Figure 1B:
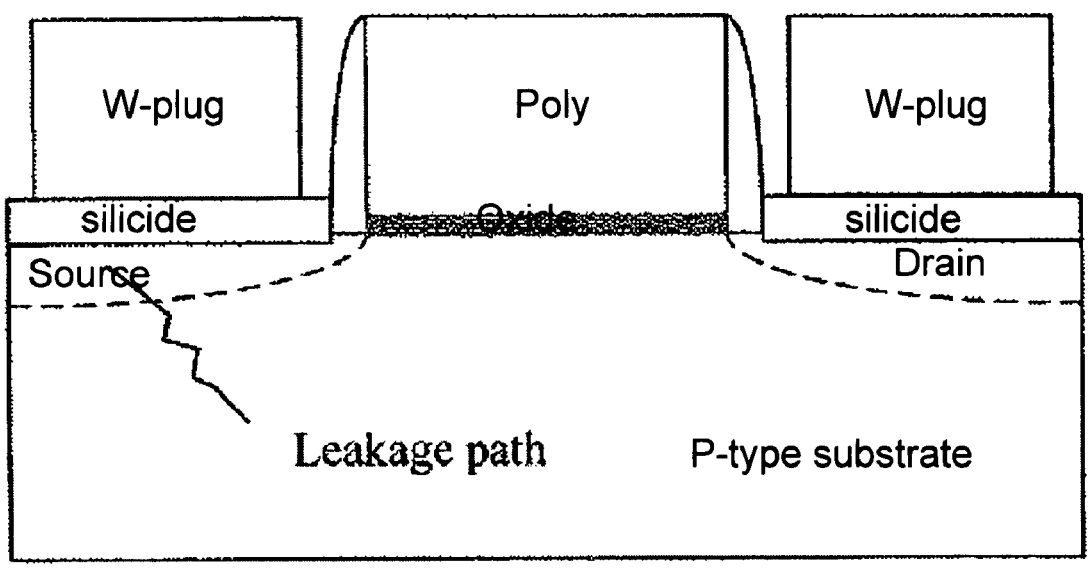
FIG. 1B is a cross-sectional diagram of a first defective NMOS structure.

Now, consider the defective NMOS structure shown in FIG. 1B, where there is a leakage path from the source to the substrate, and therefore the source is grounded. When a comparison is made between the source of the defective NMOS structure of FIG. 1B ("the target") and the source of the non-defective NMOS structure of FIG. 1A ("the reference"), voltage contrast is expected due to the surface voltage modulation by the leakage path of the target.

Figure 1C:
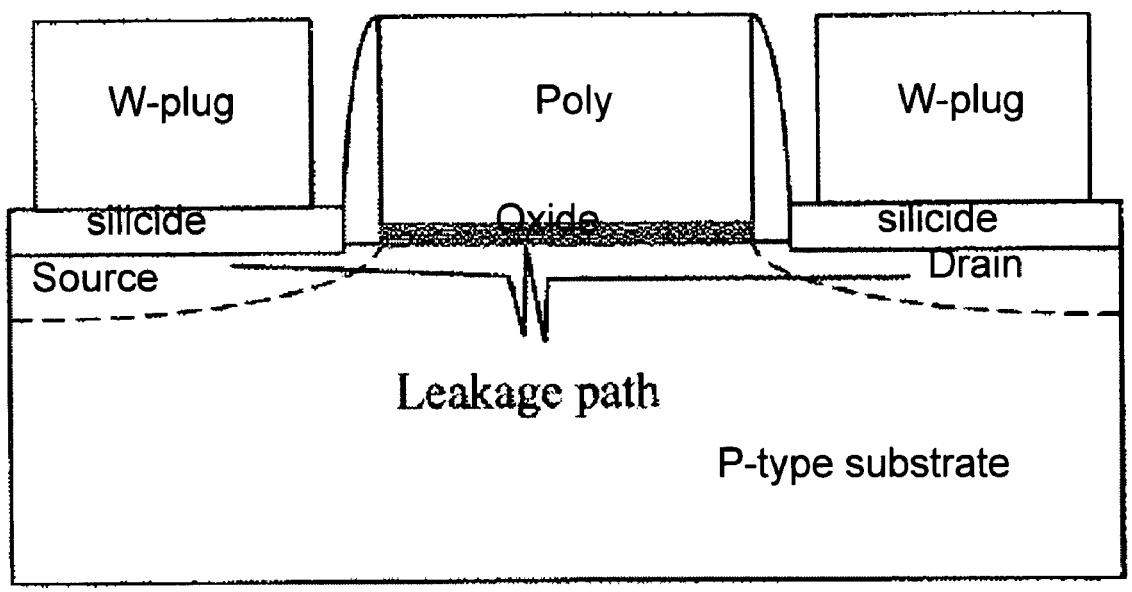
FIG. 1C is a cross-sectional diagram of a second defective NMOS structure.

Now consider a second defective structure which is shown in FIG. 1C. In this case, the leakage path is between the source and drain (rather than between the source and substrate as in FIG. 1B). Assuming that the beam is very small, similar to the W-plug size, then voltage contrast may show up at W-plugs at both source and drain when the beam hits them. This is because, in this case, both source and drain have leakage paths (to each other). However, such voltage contrast at both source and drain may also be caused by both source and drain each having a leakage path to the substrate.

One problem with conventional voltage contrast is that it may be difficult in some cases to distinguish between the various possible defects. For example, conventional voltage contrast may have difficulty distinguishing between a leakage path between the source and drain (as in FIG. 1C) and leakage paths from both source and drain to the substrate (similar to FIG. 1B).

Furthermore, in the case of FIG. 1C, conventional voltage contrast due to the leakage path may be faint and difficult to see. This is because charge build-up is still occurring despite the defect, although the build-up is expected to be slower due to the sharing of charge between the source and drain.

The present application discloses a method and apparatus for voltage contrast defect detection which advantageously enables suppression of "background noise" and isolation of the signal from the defect-of-interest (DOI). As disclosed herein, background suppression and DOI signal isolation may be accomplished by incorporating the response time of the structure of interest, both non-defective and defective, into the inspection scanning conditions and parameters. In particular, the method disclosed herein includes manipulation of the inspection time delay and examination of the response of the voltage contrast to facilitate identification of the DOI. As such, the method disclosed herein may be termed as "transient contrast."

When an electron beam with current $i^0$ is injected into a specimen, the electron influx and outflow are not always equal to each other. This disparity may be expressed by the following inequality.

$$\eta + \xi \neq 1 \quad \text{(Equation 1)}$$

$\eta$ and $\xi$ are the secondary and backscattering electron yields, respectively, of a specific material at a specific incident beam energy.

The consequence of this inequality depends upon the electrical characteristics and structure of the specimen. If the target is an insulator or a piece of floating conductor, then negative charge build-up will occur where the incident beam impinges upon the target. On the other hand, if the target is a grounded conductor, then the charge will be dispersed so that the system remains electrically neutral.

For example, consider grounded copper (a conductor) and an incident beam energy of 1 keV. Under those conditions, the secondary and backscattering yields have been measured at 1.33 and 0.43, respectively. This implies that for each incident electron, there are approximately 1.76 electrons being ejected out of the copper specimen.

In the case of charge build-up, the outflow may also take place through leakage i', so that the charge build-up rate $\Delta q/\Delta t$ may be expressed as follows.

$$\Delta q/\Delta t = (\eta + \xi - 1)i^0 - i' \quad \text{(Equation 2)}$$

In a simple circuit consisting of a capacitor and resistor, Equation 2 may be rearranged into the following equation.

$$\Delta V = (\eta + \xi - 1)i^0 \Delta t/C - V\Delta t/RC \quad \text{(Equation 3)}$$

In Equation 3, C represents the capacitance of the structure in question, and R represents the leakage resistance of that structure. Equation 3 is a differential equation with an analytical solution depending on initial and boundary conditions. However, because the secondary electron yield is a function of surface voltage, i.e. $\eta = \eta(V)$, it is difficult to solve this equation explicitly.

Nevertheless, applicants have made the observation that the time constant RC plays a role in the kinetics. This is especially true during the discharging process, after the incident electron beam is shut down or moved away from the point of interest. A structure with a small RC tends to restore its original (fresh) state quickly. The transient period from the charged state to the neutral state is brief for structures with small RC. In contrast, a structure with a large RC responds more slowly. It tends to keep its current (modified) state, and discharging takes a longer period of time to complete.

As disclosed herein, the above observation has significant implications for high-speed scanning and inspection. Consider that the scanning process may be viewed as a space-to-time conversion. During the inspection, the wafer is not observed all at the same time.

For example, assuming a scan is performed at 200 mega pixels per second (MPPS), the time delay between two sequential pixels in the scan is 5 nanoseconds (ns). Based on the above discussion, the 5 ns time delay may or may not have a substantial impact upon the inspection result. The extent of the impact of the time delay is determined by the RC time constant of the structure in question.

For example, consider the structure in question to be a tungsten plug of size Φ connected to a reversely biased p-n junction. The structure may be characterized by R, defined by the leakage path of least resistance either through the sidewall or junction to the substrate, and C, defined by the sum of sidewall junction and p-n junction capacitance. Here, the tungsten plug is floating such that R is large, so the time constant RC is also large. If the pixel size φ is a fraction of the plug size Φ, then it takes multiple pixels to cover one plug. Assuming that the time constant RC is much larger than the time delay between two sequential pixels, then a substantial brightness difference (contrast) may be observed between the two sequential pixels. In particular, the first pixel may appear brighter since it is observing the plug starting from its "fresh" neutral state, while the second (later) pixel may appear darker since it is observing the same plug starting from a charged state. In other words, the structure has been charged up at the commencement of sampling for the second pixel. The observed contrast is transient in nature and is dependent on the RC time constant and scan time delay. Hence, applicants use the term "transient contrast" for this observed contrast.

The present application relates to the manipulation of this transient contrast. One way to manipulate transient contrast is through scan rate tailoring. For example, a structure with an RC constant many times larger than 5 ns may not exhibit any transient contrast at all at a 200 MPPS scan rate. However, the transient contrast will reemerge if the scan rate is reduced substantially. However, because a reduction in scan rate typically translates into a reduced throughput for an inspection apparatus, it is typically undesirable to make such a reduction in scan rate. Therefore, in many cases it would be beneficial to develop a method for manipulating the transient contrast without compromising (reducing) the scan rate.

The present application discloses a technique of manipulating transient contrast without compromising (reducing) the scan rate. This technique involves, among other aspects, the careful selection of the scan direction relative to the structure of interest.

For example, assume a swath or scan line that is 1,024 pixels long, and a scan rate at 200 MMPS. The time delay between two sequential pixels on the same line is 5 nanoseconds, while the time delay between two adjacent pixels on adjacent scan lines is about a thousand times longer or about 5 microseconds (μs). One aspect of the present invention involves varying the time delay between two pixels by varying a scan direction. For example, the scan direction may be changed by wafer rotation.

In accordance with embodiments of the present invention, manipulation of transient contrast through multiple scans and wafer rotation is found to be useful in isolating and identifying a leakage path of interest and potentially the defect of interest.

Figure 2:
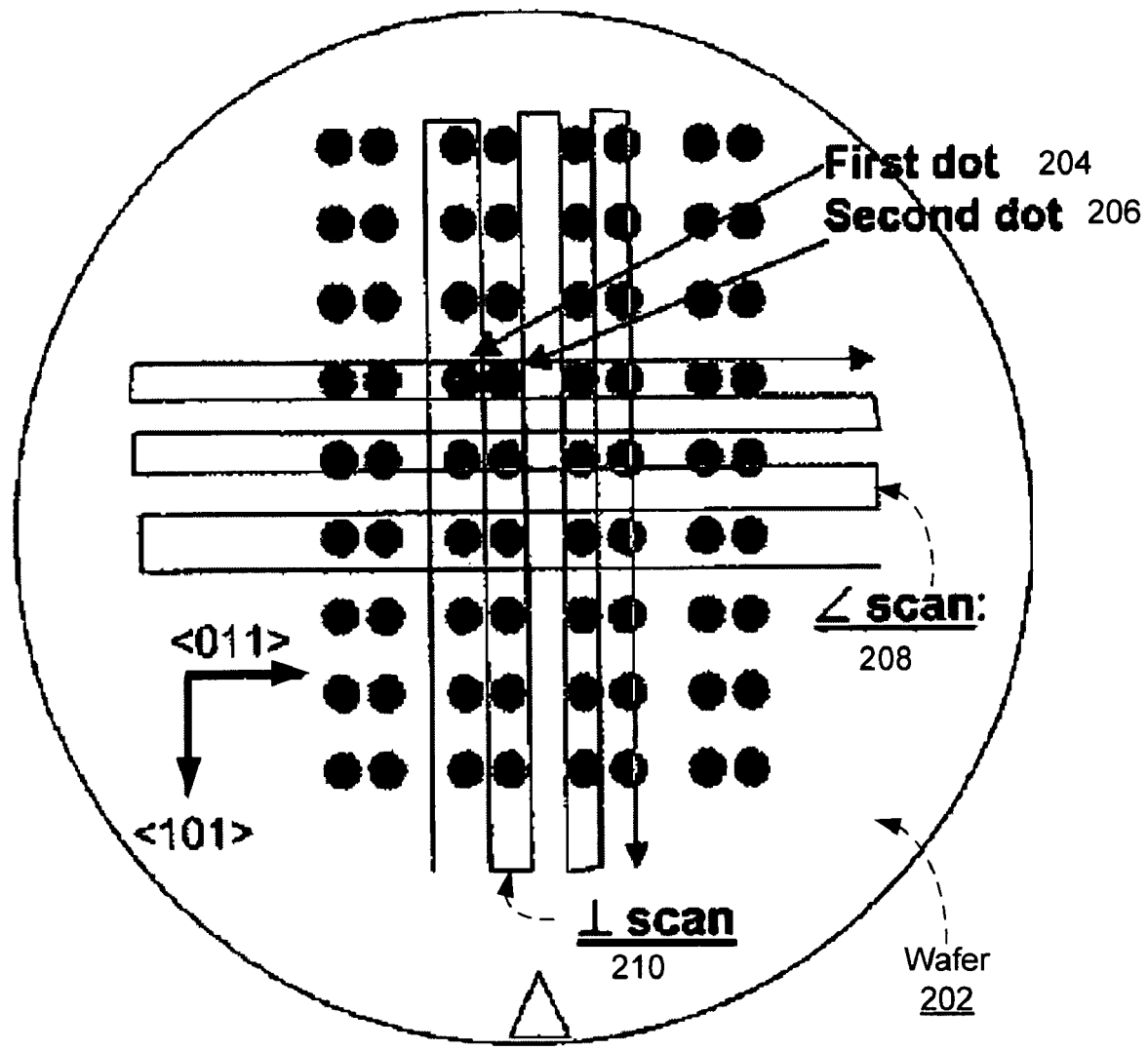
FIG. 2 is a top view schematic diagram depicting a technique for manipulating a scan rate for an example substrate in accordance with an embodiment of the invention.

An example is schematically shown in FIG. 2. Here, we assume for illustrative purposes that n-MOS devices are fabricated on a p-type (100) substrate 202 with the channel aligned toward <011> direction. Each n-MOS is then represented by an equivalent circuit consisting of two identical diodes with W plugs, represented by the first 204 and second 206 dots in FIG. 2 with the gate being omitted. The diodes are reversely biased due to the charging process. A good MOS has two diodes isolated from each other, while the defective MOS has a short between the two diodes.

In this example, we may define a scan along the <011> direction as a parallel scan 208, and a scan along the <101> direction as a perpendicular scan 210. The scan rate may chosen in such a way that the time delay between the two W plugs (204 and 206) of a same transistor is close to or smaller than the equivalent circuit RC.

In this way, the parallel scan 208 will result in the first dot being brighter than the background because the charge buildup is dispersed among two capacitors instead of one. Meanwhile, the second dot will hardly show any voltage contrast against the background because the discharging is slow. This is due to the scan time delay between the two W plugs (204 and 206) of a same transistor being close to or smaller than the RC time delay of the transistor.

On the other hand, the perpendicular scan 210 will result in both dots being brighter than the background because the scan time delay is now large enough to make the discharging complete. This is due to the scan time delay between the two W plugs (204 and 206) of a same transistor being many times larger for perpendicular scanning 210 compared to the parallel scanning 208.

In either case, it is very difficult to isolate the root-cause of the observed contrast using just one of the scans. Any leakage such as junction to the substrate could give rise to the observed voltage contrast as well.

However, in accordance with an embodiment of the invention, by combining the parallel and perpendicular scans, one is able to separate defects that do not feature the traits described. In this way, it becomes possible to identify the defects associated with the leakage path along a particular direction, along the source-to-drain direction in the current case, although the leakage path may or may not be physically visible.

Figure 3:
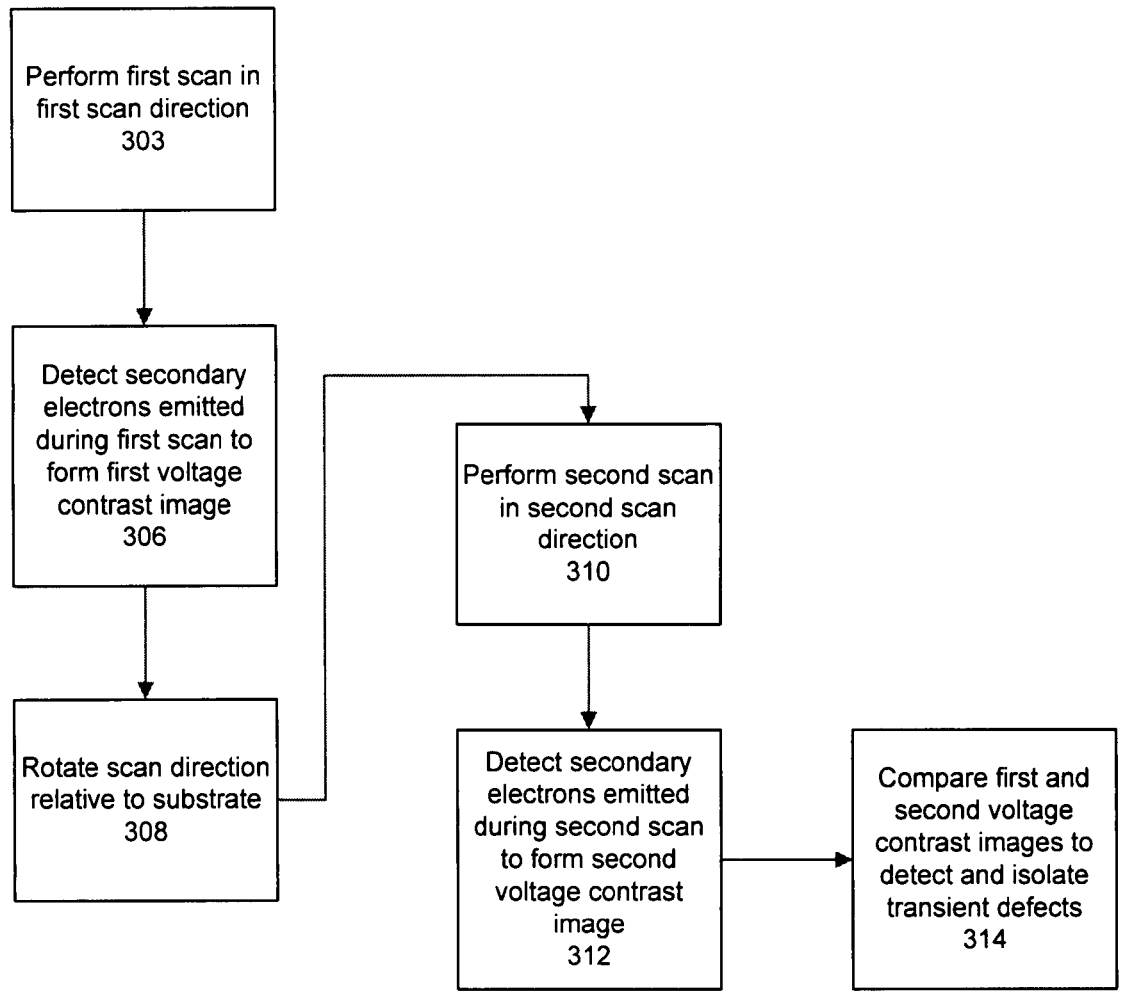
FIG. 3 is a flow chart depicting a method for detecting defects using transient contrast in accordance with an embodiment of the invention.

FIG. 3 is a flow chart depicting a method 300 for detecting defects using transient contrast in accordance with an embodiment of the invention.

A first scan is performed 303 in a first scan direction. Secondary electrons emitted during the first scan are detected 306 to form a first voltage contrast image.

Subsequently, rotation may be performed 308 so as to change the scan direction relative to the substrate. A second scan is then performed 310 in a second scan direction. Secondary electrons emitted during the second scan are detected 312 to form a second voltage contrast image.

Thereafter, data from the first and second voltage contrast images may be compared 314. The comparison allows for the detection and isolation of defects using transient contrast.

For example, consider the example depicted in FIG. 2, where there is a short circuit defect between a pair of diodes for a transistor. Further assume that the scan time delay between the two diodes of a pair for the parallel scan 208 is shorter or much shorter than the discharging time, and that the scan time delay between the two diodes of a pair for the perpendicular scan 210 is longer or much longer than the discharging time.

In this example, consider the first scan 303 as the parallel scan 208. For the first scan, the first plug 204 of the defective pair (the plug scanned first) may be brighter than the background due to charge build-up being dispersed between two capacitors, instead of one, due to the short circuit. The reduced charge build-up due to the dispersion causing the brighter pixels. On the other hand, the second plug 206 scanned shortly thereafter may hardly show any voltage contrast against the background because the charge build-up evens out and the discharging is relatively slow.

Now consider the second scan 310 as the perpendicular scan 210. For the second scan, the first 204 and second 206 plugs of the defective pair both may be both brighter than the background. This is because the first plug is scanned in a "fresh" state and the short circuit disperses the charge build-up between two capacitors, instead of one. Before the second plug 206 is scanned, the charge build-up is discharged. This is because the scan time delay between the two diodes of a pair for the perpendicular scan 210 is longer or much longer than the discharging time. Hence, the second plug is also scanned in a "fresh" state and the short circuit disperses the charge build-up between two capacitors, instead of one.

By comparing the data from the parallel and perpendicular scans, short circuit defects between two neighboring plugs may thus be determined.

Figure 4:
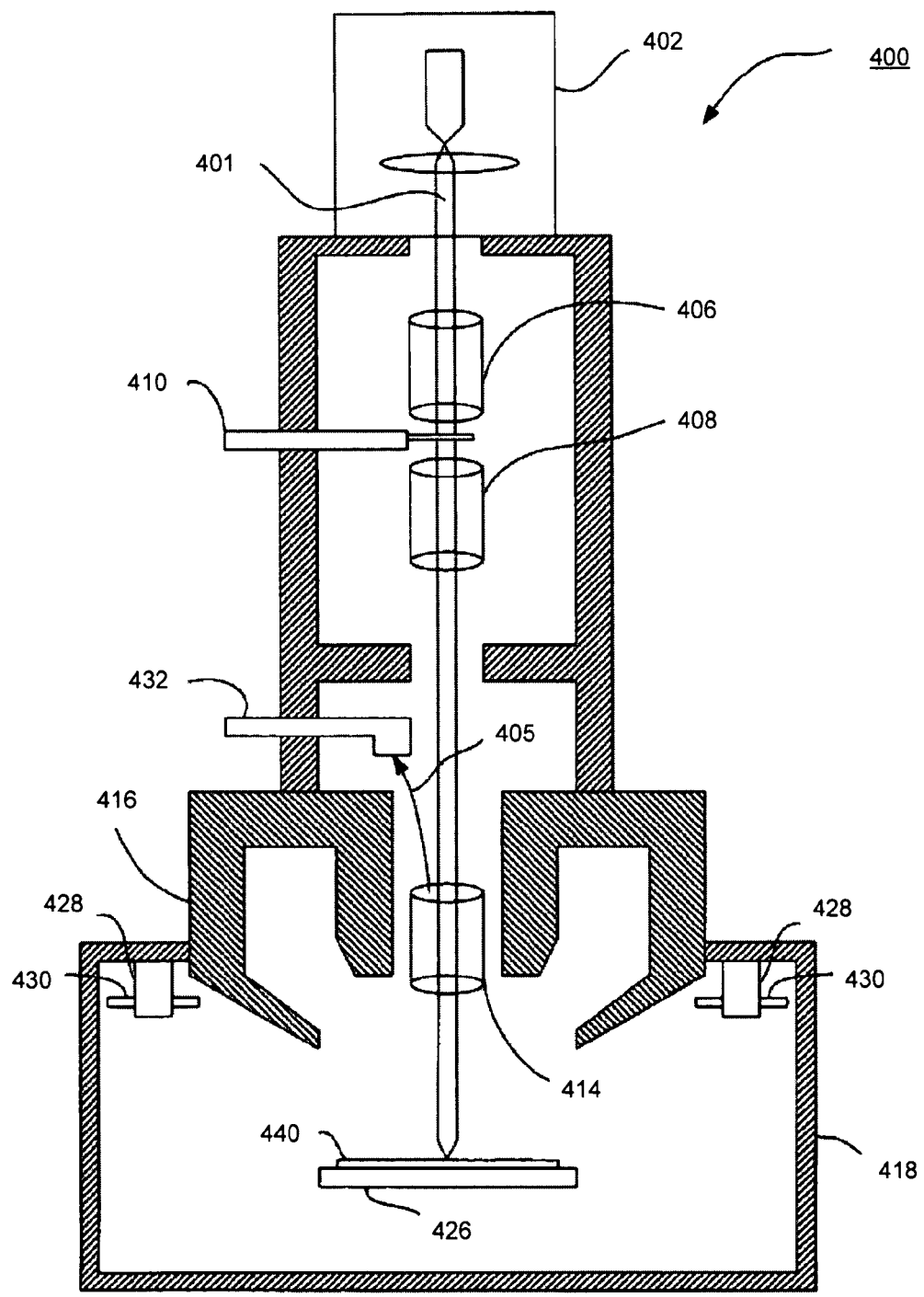
FIG. 4 illustrates a diagrammatic representation of a scanning electron microscope (SEM) in accordance with one embodiment of the present invention.

FIG. 4 illustrates a diagrammatic representation of a scanning electron microscope (SEM) 400 in accordance with one embodiment of the present invention. Of course, other SEM configurations may also be utilized. As shown, SEM system 400 includes an electron beam generator (402 through 416) that generates and directs an electron beam 401 substantially toward an area of interest on a specimen 440, which is supported by a stage 426. Specimen 400 and stage 426 are enclosed within a vacuum chamber 418.

Electron flood guns 428 may be positioned above specimen 440. Electron flood guns 428 are devices capable of directing an electron beam towards and applying electrons onto specimen 440, which may be a semiconductor wafer. The amount of charge on the wafer may be controlled using flood guns 428. The amount of charge on specimen 440 may be obtained with further assistance of an optional sample charge electrode 430. The optional specimen charge electrode 430 is positioned above specimen 440. Specimen charge electrode 430 may be maintained at a certain bias level in order to regulate the amount of charge on the surface of specimen 440. Specimen charge electrode 430 may be what is commonly referred to as a Wehnelt electrode. A biased sample stage 426 may also be used together with flood guns 428 to obtain the surface charge of specimen 440.

System 400 may operate to apply a negative or a positive charge on specimen 440 depending upon the types of voltage contrast defects desired to be reviewed. A negative charge is applied by flooding specimen 440 with electrons. Two optional and additional techniques can be used to obtain and regulate the amount of negative charge on specimen 440. First, specimen charge electrodes 430, which are located above specimen 440 are negatively biased such that secondary electrons generated during flooding with flood guns 428 are forced to remain on specimen 440. Or secondly, stage 426 may be positively biased so that secondary electrons generated during flooding are "held" onto specimen 440 from below. A positive charge is produced on specimen 440 by positively biasing specimen charge electrodes 430 or negatively biasing stage 426. In this manner, electrons are forced away from specimen 440 to leave a positively charged specimen.

SEM system 400 also includes at least one detector 432 arranged to detect charged particles 405 such as secondary electrons and/or backscattered electrons that emanate from sample 440. SEM system 400 may also detect X-rays emitted from specimen 440. Detector 432 may take the form of a micro-channel plate, micro-sphere plate, semiconductor diode, a scintillator/photomultiplier (PMT) assembly, an Energy Dispersive System (EDS), or a wavelength dispersive system (WDS) detector.

Electron beam generator (402 through 416) may be arranged in any suitable configuration for generating an electron beam that will reach specimen 440 and result in secondary electrons being emitted from the sample 440. In one embodiment, the electron beam generator can include an electron source unit 402, an alignment octopole 406, an electrostatic predeflector 408, a variable aperture 410, a Wien filter 414, and a magnetic objective lens 416. The source unit 402 may be implemented in any suitable form for generating and emitting electrons. For example, the source unit 402 may be in the form of a filament that is heated such that electrons within the filament are excited and emitted from the filament. Typical review SEM electron beams are generated at relative low current levels in order to achieve high resolution review. For instance, review SEM electron beams can be generated in the current range of 10 to 50 picoAmps. Typical electron beam spot sizes range from 2 to 20 nm.

SEM system 400 may also include an image generator (not shown) arranged to receive the detected signal and generate and/or store an image. The image generator is operable to generate an image based on the detected signal. Thus, the SEM system 400 may also include an analog to digital converter for converting the detected signal into a digital signal. The SEM system 400 may also include a computer system for processing the image frame data to generate an image of the sample. For example, successive image frame data may be averaged together to create the image.

System 400 can be arranged to review semiconductor wafers inline or offline with semiconductor manufacturing processes. Inline techniques refer to review that takes place immediately after each manufacturing process stage. Economy of time and resources can be achieved with inline techniques since defects can be located and reviewed before completion of the manufacturing processes.

In the above description, numerous specific details are given to provide a thorough understanding of embodiments of the invention. However, the above description of illustrated embodiments of the invention is not intended to be exhaustive or to limit the invention to the precise forms disclosed. One skilled in the relevant art will recognize that the invention can be practiced without one or more of the specific details, or with other methods, components, etc. In other instances, well-known structures or operations are not shown or described in detail to avoid obscuring aspects of the invention. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined by the following claims, which are to be construed in accordance with established doctrines of claim interpretation.

What is claimed is:

1. A method for detecting defects in circuitry formed on a semiconductor substrate, the method comprising:
    performing a first scan of said circuitry by scanning a primary electron beam in a first scan direction relative to said circuitry;
    detecting secondary electrons emitted during the first scan so as to form a first voltage-contrast image;
    performing a second scan of said circuitry by scanning the primary electron beam in a second scan direction relative to said circuitry, wherein the second scan direction is non-parallel to the first scan direction;
    detecting secondary electrons emitted during the second scan so as to form a second voltage-contrast image; and
    comparing the first and second voltage-contrast images to detect electrically-active defects.

2. The method of claim 1, wherein the first and second scan directions are perpendicular or nearly perpendicular to each other.

3. The method of claim 2, wherein said circuitry includes a plurality of rows of devices, and wherein the first and second scan directions are perpendicular and parallel to the rows.

4. The method of claim 1, wherein a short circuit defect is detected, and further wherein an orientation of the short circuit defect is determined.

5. The method of claim 1, further comprising:
    rotating the substrate between the first and second scans to change a direction of scanning relative to the substrate.

6. The method of claim 1, further comprising:
    using scan electronics for changing a direction of scanning relative to the substrate.

7. An electron beam apparatus for detecting defects in circuitry formed on a semiconductor substrate, the apparatus comprising:
- an electron source for generating a primary electron beam;
- a lens system configured to focus the primary electron beam onto a surface of a target substrate;
- a beam deflector configured to controllably deflect the primary electron beam;
- a detector configured to detect scattered electrons emitted from the target substrate; and
- control electronics configured to perform a first scan by scanning the primary electron beam in a first scan direction relative to the target substrate such that a first voltage-contrast image is detected, perform a second scan by scanning the primary electron beam in a second scan direction relative to the target substrate such that a second voltage-contrast image is detected, wherein the second scan direction is non-parallel to the first scan direction; and
- a data processor configured to compare the first and second voltage-contrast images to detect electrically-active defects.

8. The apparatus of claim 7, wherein the first and second scan directions are perpendicular or nearly perpendicular to each other.

9. The apparatus of claim 8, wherein the target substrate includes a plurality of rows of devices, and wherein the first and second scan directions are perpendicular and parallel to the rows.

10. The apparatus of claim 7, wherein a short circuit defect is detected by the data processor, and further wherein an orientation of the short circuit defect is determined by the data processor.

11. The apparatus of claim 7, further comprising:
- a substrate rotation mechanism for controllably rotating the target substrate between the first and second scans to change a direction of scanning relative to the target substrate.

12. The apparatus of claim 7, wherein the control electronics is configured to controllably change a direction of scanning relative to the target substrate.

13. An apparatus for detecting defects in circuitry formed on a semiconductor wafer, the method comprising:
- means for performing a first scan of said circuitry by scanning a primary electron beam in a first scan direction relative to said circuitry;
- means for detecting secondary electrons emitted during the first scan so as to form a first voltage-contrast image;
- means for performing a second scan of said circuitry by scanning the primary electron beam in a second scan direction relative to said circuitry, wherein the second scan direction is non-parallel to the first scan direction;
- means for detecting secondary electrons emitted during the second scan so as to form a second voltage-contrast image; and
- means for comparing the first and second voltage-contrast images to detect electrically-active defects.

* * * * *